United States Patent [19]
Grenier

[11] Patent Number: 6,123,078
[45] Date of Patent: *Sep. 26, 2000

[54] RADIONUCLIDE ANGIOGRAPHIC COLLIMATOR SYSTEM

[75] Inventor: Raymond P. Grenier, Milwaukee, Wis.

[73] Assignee: Picker International, Inc., Cleveland, Ohio

[*] Notice: This patent is subject to a terminal disclaimer.

[21] Appl. No.: 08/155,468

[22] Filed: Nov. 19, 1993

Related U.S. Application Data

[63] Continuation of application No. 07/605,722, Oct. 29, 1990, Pat. No. 5,309,911.

[51] Int. Cl.[7] .............................. A61B 6/00; H01J 35/00
[52] U.S. Cl. ...................... 128/653.1; 250/363.1; 250/503.1; 250/505.1; 378/149; 976/DIG. 429
[58] Field of Search ................... 128/653.1, 659; 250/363.1, 496.1, 503.1, 505.1; 378/113, 145, 147, 149, 154; 976/DIG. 429, DIG. 430, DIG. 428

[56] References Cited

U.S. PATENT DOCUMENTS

| | | | |
|---|---|---|---|
| 4,125,776 | 11/1978 | Tosswill et al. | 378/149 |
| 4,825,454 | 4/1989 | Annis et al. | 378/147 |
| 5,099,134 | 3/1992 | Hase et al. | 250/505.1 |
| 5,309,911 | 5/1994 | Grenier | 128/653.1 |

*Primary Examiner*—Krista M. Zele
*Attorney, Agent, or Firm*—Reinhart, Boerner, Van Deuren, Norris & Rieselbach, s.c.

[57] ABSTRACT

A gamma ray collimator for use in a cardiac inspections system is disclosed which resolves energetically unperturbed gamma rays emitted from a patient and removes inelastic scattered gamma rays. A plurality of collimator elements each have walls, with each wall defining a plane comprised of a first material layer covered by a second material layer and absorbing inelastic scattered gamma rays, the planes being parallel to a central longitudinal axis in each of the collimator elements. The walls of each collimator element define an elongated longitudinal passageway having open ends through which the energetically unperturbed gamma rays enter and leave. The first material layer has a large absorption coefficient for gamma rays, and the second material layer has a large absorption coefficient for inelastically scattered gamma rays generated in the first material layer responsive to gamma rays emitted from the patient.

16 Claims, 12 Drawing Sheets

| B SVC 0.75 | RA 1.5 | RA RAV 2.25 | RA RV PA 3.0 | RH RL 3.75 | PA RL LL 4.5 | PA L 5.25 |
|---|---|---|---|---|---|---|
| PA L 6.0 | L 6.75 | L 7.5 | L LA 8.25 | L LA LV 9.0 | L LA LV 9.75 | LA LV AO 10.5 |
| LV AO AT 11.25 | LV AO AT 12.0 | LV AO AT 12.75 | LV AO DA 13.5 | LH 14.25 | LH 15.0 | LH 15.75 |
| LH 16.5 | LH 17.25 | LH 18.0 | LH MY 18.75 | LH MY 19.5 | LH RH 20.25 | LH RH 21.0 |
| RC 21.75 | RC 22.5 | RC 23.25 | RC 24.0 | RC 24.75 | RC 25.5 | RC 26.25 |

RADIONUCLIDE ANGIOGRAPHIC COLLIMATOR SYSTEM

This is a continuation of application Ser. No. 07/605,722, now U.S. Pat. No. 5,309,911, filed on Oct. 29, 1990.

BACKGROUND OF THE INVENTION

This invention is generally concerned with an angiographic collimator for removing unwanted divergent beams of radiation received from a radionuclide source, leaving a well resolved radiation beam for detection and analysis of a patient's cardiac system. More particularly, the invention is directed to an angiographic collimator having a layered wall structure for removing not only unwanted angularly divergent gamma radiation beams, but also for removing gamma radiation inelastically scattered by the collimator structure itself enabling improved analysis of a patient's cardiac system.

Angiographic imaging methods and apparatus are undergoing rapid evolution as efforts are being made to improve the ability to image selected internal portions of the human cardiac system. The effectiveness of these various imaging methodologies, and even the ability to use certain imaging techniques for effective clinical diagnosis of the cardiac system, depends primarily on spatial resolution and on the associated signal to noise ratio in the data being accumulated. Present angiographic technology is able to generate in a manner safe to a patient, a gamma radiation intensity adequate to image a number of abnormalities in the heart and the associated cardiac system. However, current technology cannot effectively collimate this gamma radiation intensity without counting certain divergent radiation and thus including substantial unwanted noise in the resulting data. Such divergent, unwanted signal derives, for example, from radiation which has been inelastically scattered from the collimator structure itself. This deficiency therefore requires exposing the patient to larger intensities of gamma radiation in order to achieve a desired resolution. Unfortunately, such increased radiation exposure can increase the hazard to a patient, and moreover there are some divergent radiation sources whose deleterious effects cannot be alleviated even by increasing the radiation signal level from the patient.

It is therefore an object of the invention to provide an improved method of manufacture and method for collimation of radionuclide radiation in an angiographic inspection system.

It is another object of the invention to provide a new method of manufacture of an angiographic collimator for a gamma ray beam.

It is a further object of the invention to provide an improved angiographic collimating device for removing divergent gamma radiation and X-ray beams received from, or passed through, a patient undergoing cardiac system analysis.

It is an additional object of the invention to provide a new angiographic gamma ray collimator assembly for providing highly resolved, high intensity data characteristic of a patient but without having to increase patient exposure to gamma radiation.

It is yet another object of the invention to provide an improved angiographic radiation collimator assembly having a layered wall material structure for substantially reducing inelastic scattered X-rays present in the detected data signal.

It is still a further object of the invention to provide a new radionuclide gamma ray collimator having a lead base structure with an outer layer of a material which preferentially absorbs X-rays generated from inelastic scattering of gamma rays from the lead base collimator structure.

It is yet an additional object of the invention to provide an angiographic radiation collimator having a selectable collimator length using a stack of different predetermined height collimator units.

It is still a further object of the invention to provide an angiographic gamma ray collimator of lead with a thin tin layer on the collimator walls to absorb lead X-rays generated by inelastic gamma ray scattering from the lead collimator.

Other objects, features and advantages of the present invention will be readily apparent from the following description of the preferred embodiments thereof, taken in conjunction with the accompanying drawings described below wherein like elements have like numerals throughout the several views.

DESCRIPTION OF THE DRAWINGS

FIG. 6 shows a chart of the explanation key for each block of a matrix of time lapse photographs of a patient's cardiac system;

DETAILED DESCRIPTION OF PREFERRED EMBODIMENTS

Figure 1:
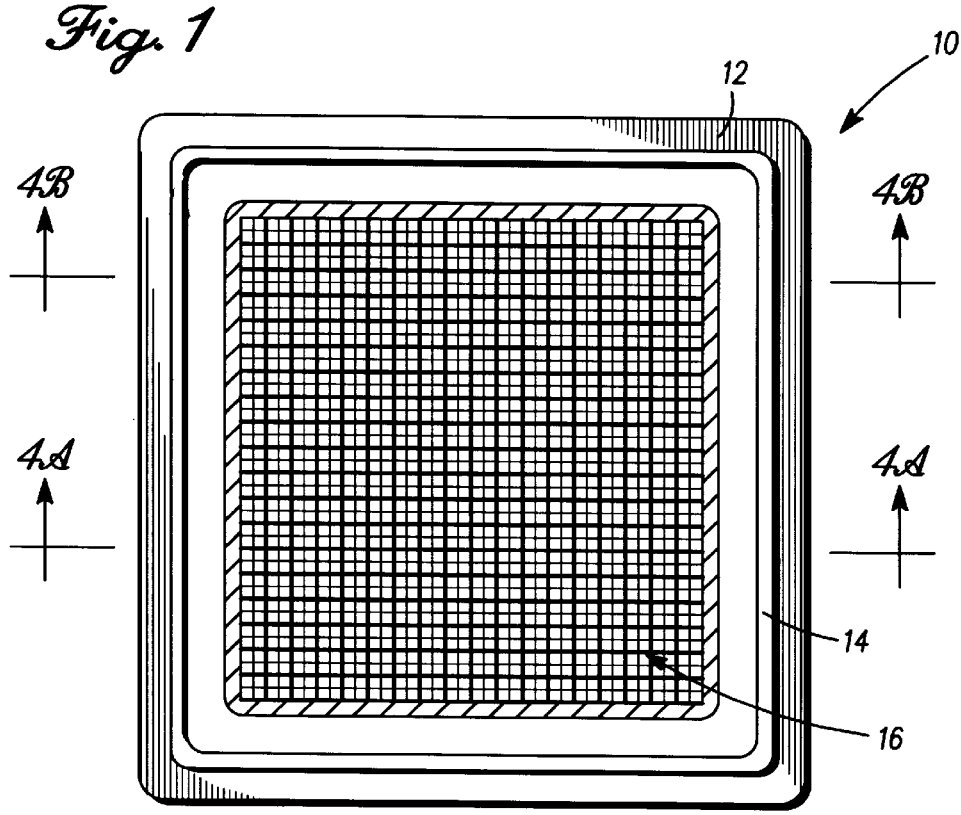
FIG. 1 shows an incident gamma radiation view of an angiographic collimator assembly.
Figure 4A:
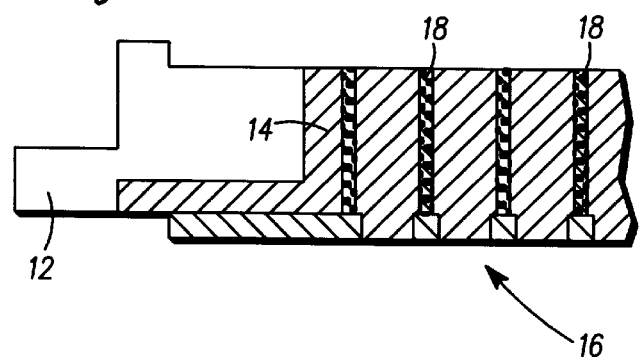
FIG. 4A shows a cross section taken along line 4A—4A in FIG. 1
Figure 4B:
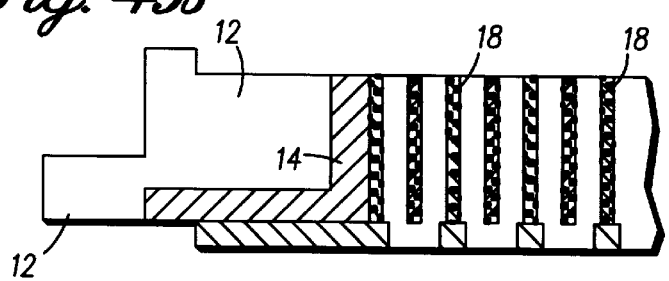
FIG. 4B shows a cross section taken along line 4B—4B in FIG. 1.

An angiographic gamma ray collimator assembly constructed in accordance with the invention is shown generally at 10 in FIG. 1. The angiographic collimator assembly 10 (hereinafter "collimator assembly 10") includes a housing 12, typically constructed of aluminum. Coupled to the housing 12 is a side shielding 14 which is normally constructed of lead when the collimator assembly 10 is used for collimation of gamma rays. Disposed within the housing 12 and coupled to the side shielding 14 are collimator elements 16 constructed of collimator walls 18 (best seen in FIGS. 2–4).

Figure 2:
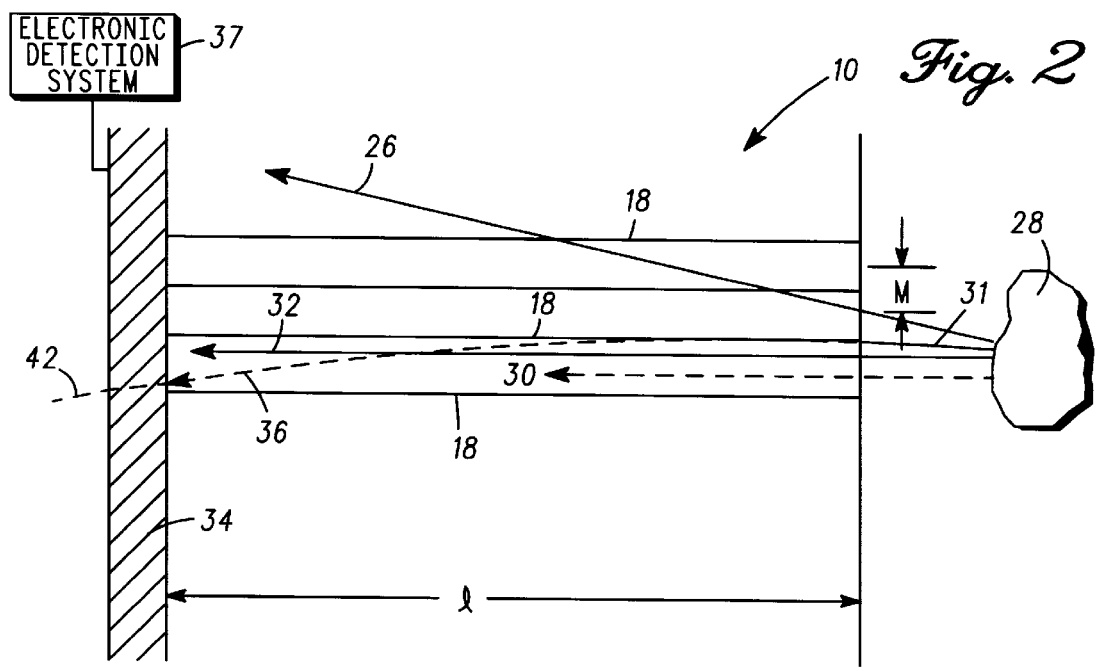
FIG. 2 shows a side view of a cross section of a single vertical stack of collimators.
Figure 3:
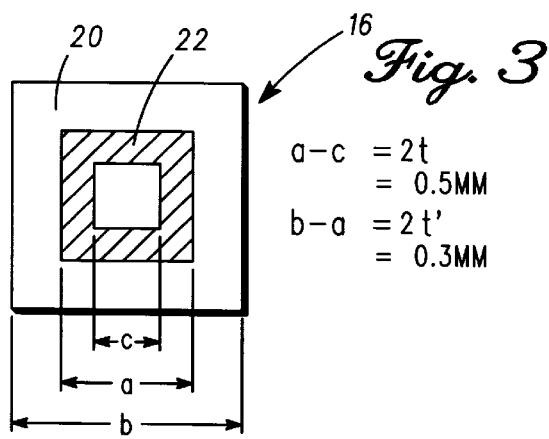
FIG. 3 illustrates a top, or face, view of one embodiment of a collimator.

In a preferred embodiment the collimator walls 18 are constructed of a layered material with a base material structure 20 and a thin layer 22 disposed thereon (see FIGS. 2 and 3). The radiation used in a conventional angiographic embodiment is gamma rays or high energy X-rays, and in a preferred embodiment the base material structure 20 is lead and the thin layer 22 is tin. For example, as shown in FIG. 3 in a preferred geometry the collimator walls 18 are square cross section tubing with lead being the base material structure 20 (hereinafter "lead structure 20") and tin being the thin layer 22. The tin can be readily coupled to the lead structure 20 by conventional methods such as electroplating, evaporation, ion deposition and mechanical lamination.

Operation of the collimator assembly 10 is best illustrated in FIG. 2. Gamma rays 26 originate from a conventional radionuclide source, such as cobalt, thallium or technitium, which is injected in a liquid form into a patient 28 (depicted schematically). The liquid radionuclide source passes through the patient's cardiac system. As the radionuclide source undergoes radioactive decay, it emits characteristic gamma rays forming a cardiac image, such as for conventional "first pass" angiography. For example, see copending patent application Ser. No. 07/409,249 assigned to the instant assignee and is incorporated by reference herein. A desired gamma ray portion 30 of the gamma rays 26 travels along a substantially parallel line 32 or in a very narrow angular range within which the gamma rays do not strike the collimator assembly 10. The desired gamma ray portion 30 thus passes undisturbed through the collimator assembly 10. This desired gamma ray portion 30 is sensed by a conventional detector 34, such as, a gamma ray counter of a conventional Anger camera or a sensor of a first pass cardiac inspection system, such as an angiographic system of Scinticor Incorporated of Milwaukee, Wis.

In addition to the desired gamma ray portion 30, having a substantially unchanged primary energy $E_0$ after emission from the radionuclide source, there is a substantial fraction of divergent gamma rays 31 from the patient 28. These divergent gamma rays 31 interact with the collimator walls 18 and result in diminished resolution of the cardiac system spatial features in the patient 28. The desirability of removing such divergent gamma rays 31 is well known. For example, in U.S. Pat. No. 4,096,389 (which is incorporated by reference herein) the benefits of effective collimation, generally, are described for gamma ray radiographic imaging technology. Such advantages are apparent for other conventional radiographic systems, such as in emission tomography systems and Anger camera geometries (see, for example, U.S. Pat. Nos. 4,295,047; 4,682,033; 4,852,142; 4,672,648; and 4,277,684, which are incorporated by reference herein).

The divergent gamma rays 31 interact with the collimator walls 18 and the divergent gamma rays 31 lose energy, creating inelastic scattered radiation 36 having energies less than $E_0$ of the initial gamma rays 26. In order to achieve optimum resolution, the divergent gamma rays 31 (and the inelastic scattered byproduct radiation) should be substantially removed by the collimator assembly 10. Removal of the inelastic scattered radiation 36 would allow sensing and analysis of only the desired gamma ray portion 30. As mentioned before this portion 30 is substantially parallel to line 32 in FIG. 2 and includes the undisturbed gamma rays 30 from the patient 28. This desired gamma ray portion 30 is then sensed by detector 34. This enables achieving the desired level of resolution for the cardiac system features of the patient 28.

As mentioned hereinbefore, the divergent gamma rays 31 before interaction with the collimator walls 18 have an energy of $E_0$, and after wall interaction the inelastic scattered radiation 36 includes a range of electromagnetic wave energies, from $E_0$ at a maximum to lesser values. In the case of an inelastic interaction, the divergent gamma rays 31 interact with the lead structure 20 of the collimator assembly 10. When the gamma rays 31 (such as cobalt radionuclide gamma ray having an energy of roughly 140 KeV) enter the lead structure 20, energy can be lost by a variety of processes. For example, energy can be lost by excitation of electrons from the ground state in each of the lead atoms. These excited electrons return to their ground state energy level and simultaneously emit a characteristic X-ray, such as Pb K-alpha radiation having an energy of about 74 KeV. Numerous other electron excitations and decays to ground state occur, giving rise to lower energy X-rays and other electromagnetic wave species which are preferentially absorbed within the lead structure 20. These events normally occur without reemitting any X-rays into the collimator free space outside the lead structure 20, and thus the lower energy radiation is not normally detected by the detector 34.

Therefore, as stated above, when the divergent gamma rays 31 enter the lead structure 20, a 74 KeV X-ray can escape into free space as a consequence of inelastic scattering of the 140 KeV cobalt gamma ray. This emitted 74 KeV inelastic scattered X-ray 36 travels along line 42 (see FIG. 2) and is sensed by the detector 34. Conventional energy discriminators in an electronic detection system 37 (shown schematically), which is coupled to the detector 34, can remove the unwanted signal arising from the inelastic scattered X-ray 36. However, such a sensed event can cause substantial loss of resolution which is detrimental to spatial resolution. This loss of resolution can result because the event is still counted by the counter 34 and prevents detection of the desired undeviated gamma ray portion 30. Conventional counter electronics in the detection system 37 can only count at a given finite rate, such as, for example, 1,000,000 counts per second, and detection of unwanted energetic photons prevents accumulating a desired event. The need to maximize useful signal and to minimize radiation exposure to the patient (coupled with the limits on the ability of the electronics to count all incoming events) makes it imperative to remove the emitted, or inelastically scattered, X-rays 36 in order to use the full capacity of the counter 34 to sense the desired gamma ray portion 30.

In FIGS. 2 and 3 is shown the layered wall structure of the collimator assembly 10. This layered wall structure enables detection of substantially only the gamma rays 30 by removal of the unwanted inelastic scattered X-rays 36 such that the component is not sensed by the detector 34. As shown in the preferred embodiment, the thin layer 22 is tin but can be any material which exhibits a large absorption coefficient for the energetic inelastic scattered X-rays 36 emitted from the underlying lead structure 20. The tin layer 22 can be quite thin (for example, about ¼ mm) and still be quite effective in absorbing the inelastic scattered lead K-alpha X-rays 36. As can be understood from conventional X-ray optics the only portion of energetic photons which might be sensed by the detector 34 is emitted primarily at relatively small angles with respect to the line 32. The geometry of the collimator assembly 10, including the length "l" in FIG. 2 and the other dimensions (see FIG. 3), result in the reemitted inelastic scattered X-rays 36 traveling over a substantial path length within the tin layer 22. As a consequence of the large path length traveled at such small angles relative to direction 32 and the well known exponential absorption attenuation, the tin layer 22 is very effective in removing the unwanted inelastic scattered X-rays 36. The ratio of transmitted intensity to initial intensity is exp $(-\mu.t)$, where $\mu$ is the well known linear absorption coefficient of tin (about 28.1 cm$^{-1}$ at 75 KeV), and "t" is the path length traveled by the inelastic scattered X-rays 36 in the tin layer.

Figure 5A:
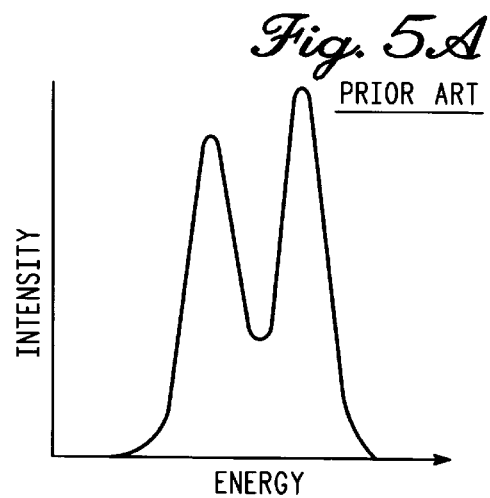
FIG. 5A illustrates the detected radiation spectra from a cobalt radionuclide source using a conventional lead collimator assembly and FIG. 5B shows the radiation spectra using the layered lead-tin collimator assembly of the invention.
Figure 5B:
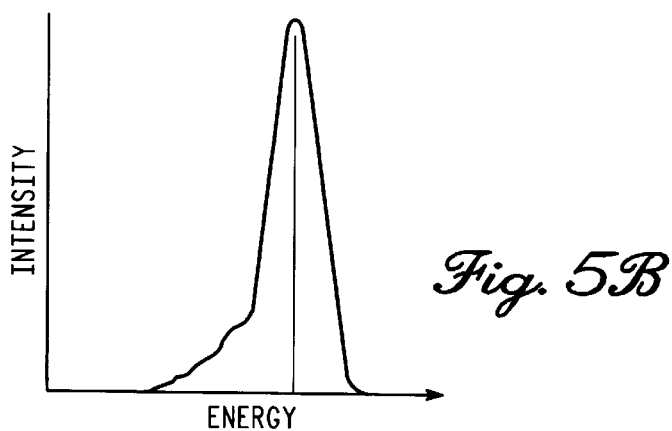

The effect of the collimator assembly 10 is demonstrated dramatically by comparing FIGS. 5A and 5B. FIG. 5A shows the radiation sensed by the detector 34 in a Scinticor angiographic system for a collimator system having only a lead base structure. As can be seen in FIG. 5A, there are two prominent peaks sensed, one peak at about 75 KeV associated with the lead K-alpha inelastically scattered X-rays 36 and a second cobalt gamma ray peak at about 140 KeV. The nearly equal prominence of the intensity of the two peaks points out the significance of removing the inelastic scattered X-rays 36. In FIG. 5B is shown the energy spectrum detected employing the collimator assembly 10 with substantially identical collimator dimensions.

As demonstrated by the data of FIG. 5, the collimator assembly 10 is highly effective in the removal of the lead K-alpha inelastic scattered X-rays 36, thus enabling the detector 34 to sense only the desired gamma ray portion 30. Consequently, the efficiency of detection for a given radionuclide source intensity in the patient 28 can be substantially enhanced. As determined by actual experiment in Scinticor angiographic systems, this improvement is about 50 percent for the illustrated embodiment, wherein the number of 140 KeV events detected increases, for example, from about 400,000 to 600,000 counts per second.

Such an improvement in counting efficiency also results in enhanced signal which manifests itself as improved image resolution of the patient's cardiac system. For example, as shown by the angiographic image data of FIGS. 6–14, a cardiologist is now able to resolve critical features previously unresolvable. The use of the collimator assembly 10 has, therefore, substantially improved resolution such that high quality first pass angiography can now be performed routinely. As shown in FIGS. 7–14, the resulting images are of high quality, enabling a cardiologist to more effectively perform diagnoses previously made without the benefit of such detailed medical information.

Figure 7:
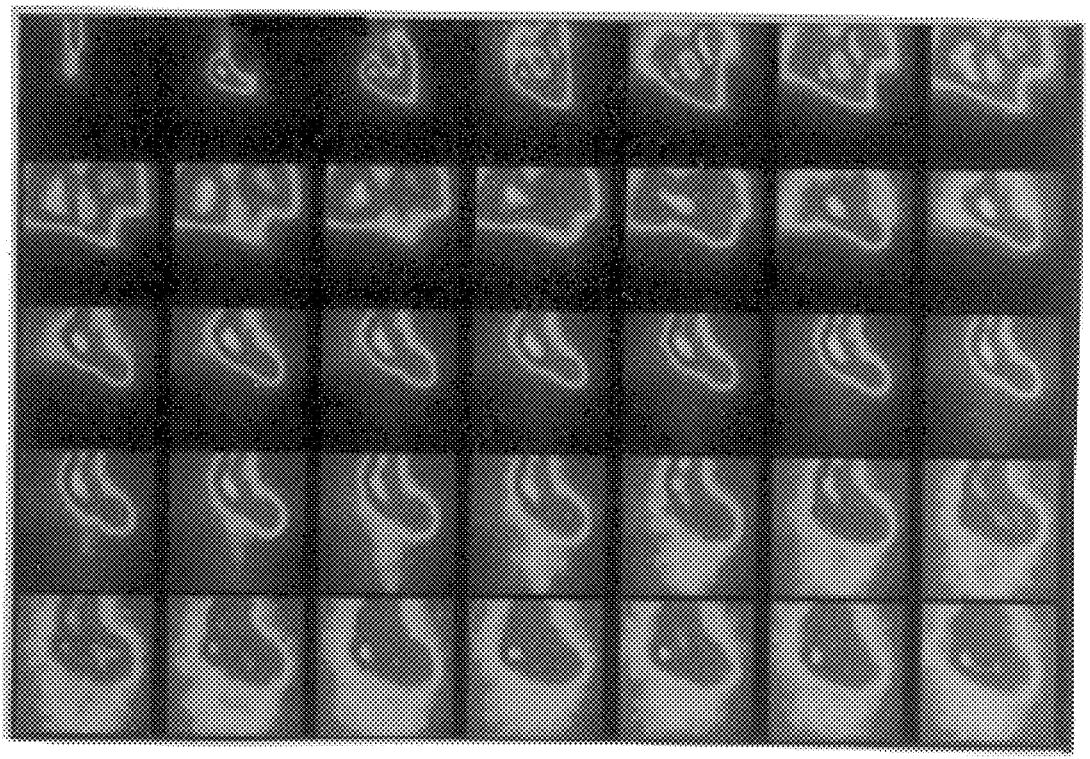
FIG. 7 shows an example time lapse photograph for a matrix of photographs of a patient's cardiac system in a radionuclide angiographic (RNA) study.

In regard to the angiographic image data, FIG. 7 shows an example time lapse photograph for each block of a matrix of time lapse photographs of a patient's cardiac system in an RNA (radionuclide angiographic) study on a SIM400. This figure illustrates passage of a bolus through the central circulation during a first pass RNA study. FIG. 6 shows the explanation key for the matrix of time lapse photographs of FIGS. 7–14, and the numbers in the lower right hand corner of FIG. 6 are elapsed time in seconds. These images are compressed by a factor of thirty times the original framing rate.

Figure 8A:
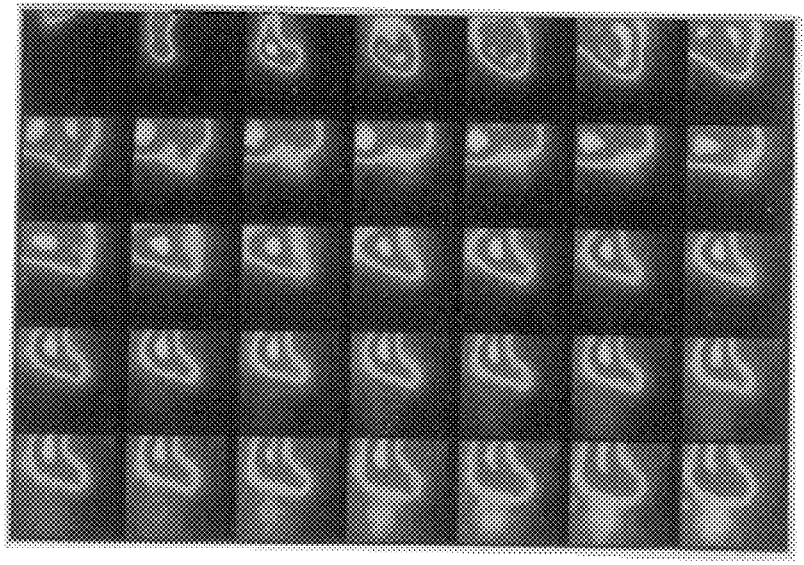
FIG. 8A shows an RNA study for a patient Beau using a conventional lead collimator and FIG. 8B shows an RNA study for patient Beau using a tin/lead collimator form of the invention.
Figure 8B:
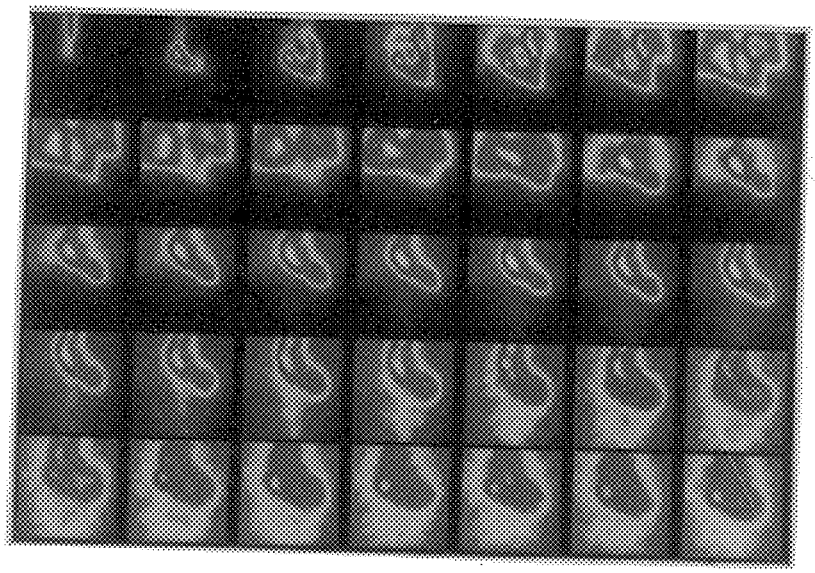

The abbreviation keys in FIG. 6 are referenced as follows:
Image Descriptions (Read from left to right and top to bottom.)
Key
 B—Bolus
 RA—Right Atrium
 PA—Pulmonary Artery
 LL—Left Lung
 L—Lungs: includes RL and LL
 LA—Left Atrium
 LV—Left Ventricle
 AO—Proximal Aorta
 AT—Aortic Outflow Track
 DA—Descending Aorta
 MY—Myocardium
 LH—Left Heart; includes LA, LV, AO, AT, DA
 RC—Recirculation: includes LH and RH
 SVC—Superior Vena Cava
 RV—Right Ventricle
 RH—Right Heart includes RA, RV, PA
 RL—Right Lung FIG. 8A is an RNA study performed Sep. 22, 1989 on patient Beau using the Conventional Lead Collimator on SIM400. FIG. 8B is another RNA study performed on patient Beau. The study was performed Sep. 18, 1990 using a research model of the Tin/Lead Collimator on SIM400. The conclusions reached are that RH, L, and LH phases are clearly better imaged with the Tin/Lead Collimator in FIG. 8B than FIG. 8A and that the LV is especially better defined in FIG. 8B. Note that the study parameters were essentially identical in both FIGS. 8A and 8B studies; these include bolus technique, dose, patient positioning, image processing, and all hardware except the collimators.

Figure 9A:
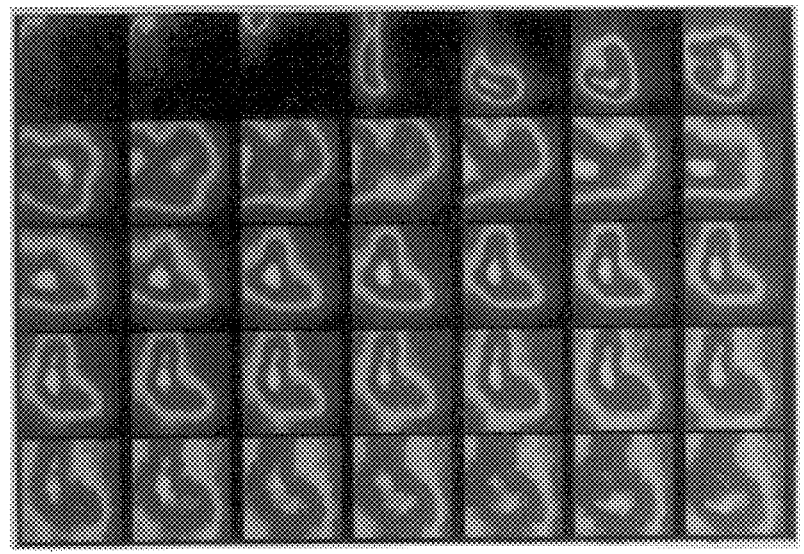
FIG. 9A shows an RNA study for a patient Cul using a conventional lead collimator and FIG. 9B shows an RNA study for patient Cul using a tin/lead collimator form of the invention.
Figure 9B:
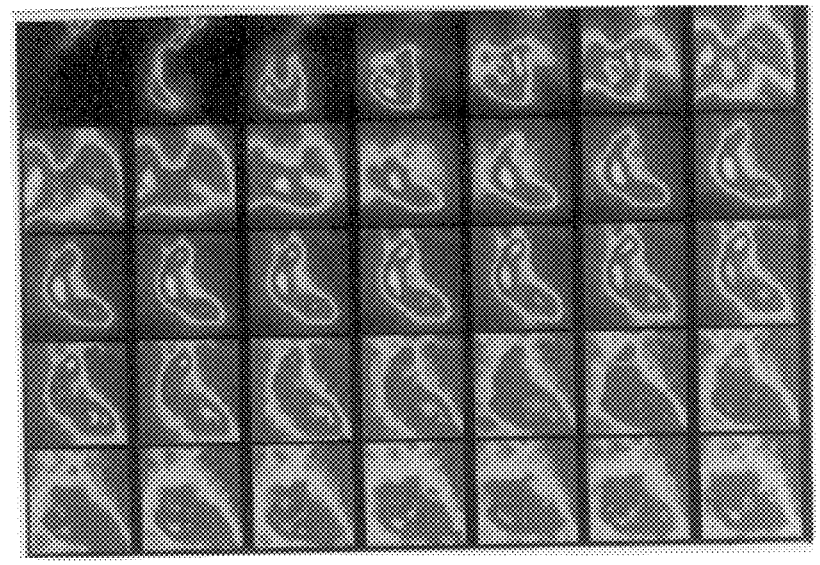

In FIG. 9A is shown data for patient Cul. An RNA study was performed on Jun. 9, 1989 using the Conventional Lead Collimator on SIM400. Another RNA study was performed on patient Cul on Sep. 5, 1990 using a research model of the Tin/Lead Collimator on SIM400 as illustrated in FIG. 9B. The study concluded (a) that the RH and LH chambers are more clearly delineated in FIG. 9B; (b) the LV, RV and PA are better resolved in FIG. 9B than 9A; and (c) the valve planes are not delineated in FIG. 9A, especially the pulmonary valve between RV and PA and the Aortic valve between LV and 40 which are clearly visualized in FIG. 9B. Note the study parameters and protocols are essentially identical in FIGS. 9A and 9B except for the collimators as indicated.

Figure 10A:
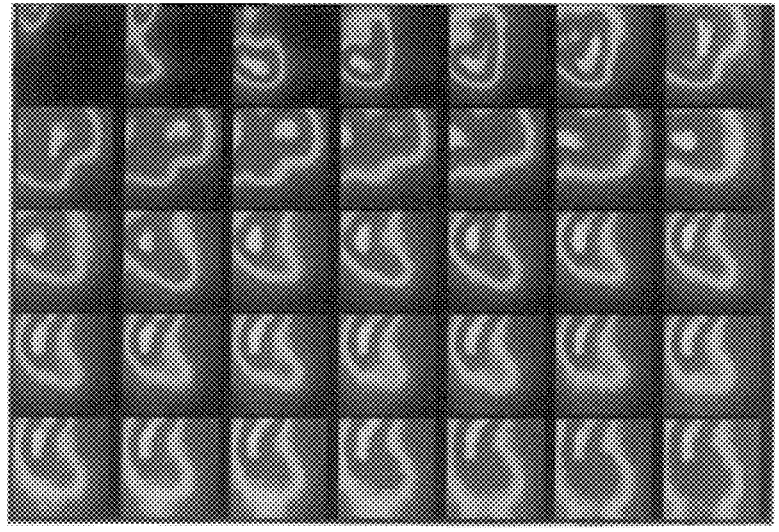
FIG. 10A shows an RNA study for a patient Rose using a conventional lead collimator and FIG. 10B shows an RNA study for patient Rose using a tin/lead collimator form of the invention.
Figure 10B:
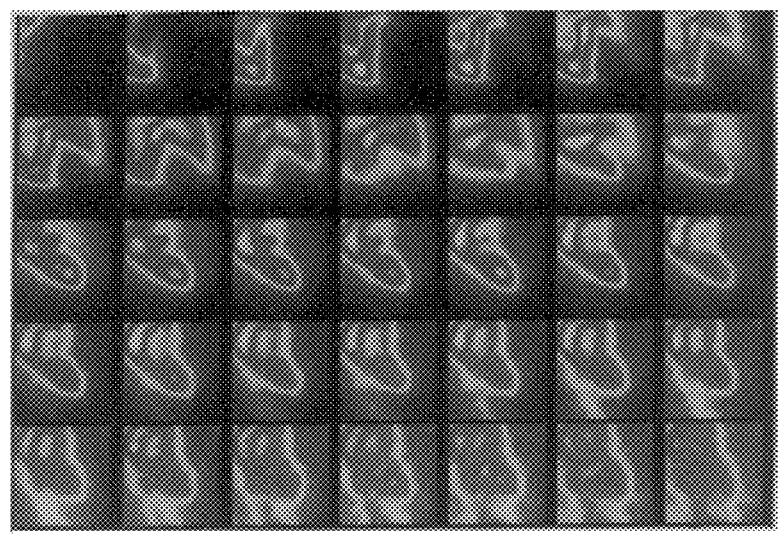

FIG. 10A illustrates the results of an RNA study performed on patient Rose on May 5, 1989 using the Conventional Lead Collimator on SIM400. Another RNA study was performed on patient Rose on Sep. 10, 1990 using a research model of the Tin/Lead Collimator on SIM400. The study concluded that (a) the LV in FIG. 10B is well visualized from the Aortic valve plane to the apex compared to FIG. 10A which merges the LV with the AO; (b) the LL in FIG. 10B is well separated from the LV chamber strongly suggesting that FIG. 10B has much reduced anatomic background and Compton scatter background compared to FIG. 10A; and (c) the AO valve plane is clearly visualized in FIG. 10B but burnt out by saturated counts in the AT in FIG. 10A. Note the study parameters and protocols were essentially identical in both RNA studies except for the collimators as indicated.

Figure 11A:
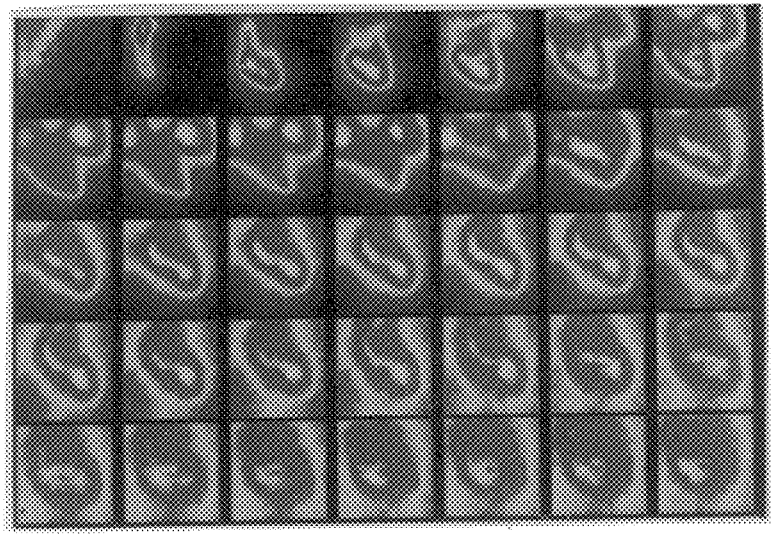
FIG. 11A shows an RNA study for a patient Badu using a conventional lead collimator and FIG. 11B shows an RNA study for patient Badu using a tin/lead collimator form of the invention.
Figure 11B:
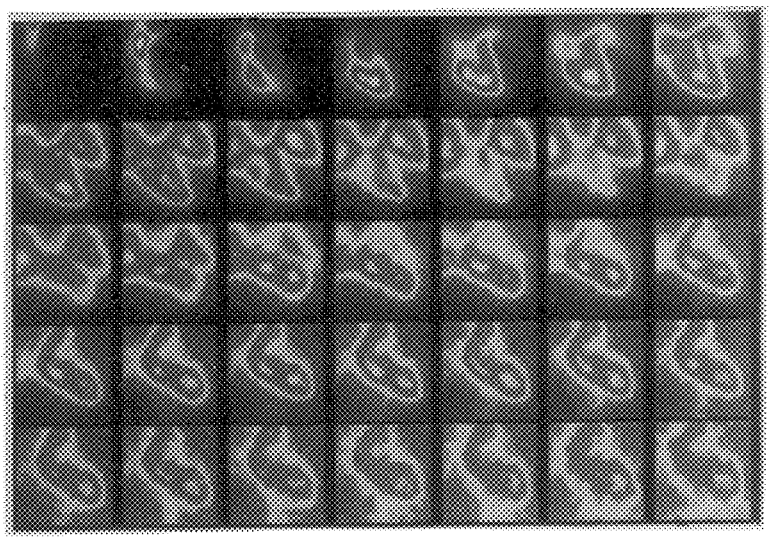

The Conventional Lead Collimator was used in an RNA study performed Jun. 21, 1989 on patient Badu illustrated in FIG. 11A. In FIG. 11B is shown data for another study on patient Badu. This figure illustrates the (-NORTH-)y study performed Aug. 22, 1990 using a research model of the Tin/Lead Collimator on SIM400. The conclusions of the study are as follows: (a) FIG. 11B clearly shows improved resolution and contrast compared to FIG. 11A; (b) the LV is better resolved in FIG. 11B; and (c) the lungs are well separated from the Right and Left Ventricular chambers in FIG. 11B compared to FIG. 11A. This leads to a 50% reduction in lung background over the LV in FIG. 11B compared to FIG. 11A. The study parameters and protocols were essentially identical in both studies of FIGS. 11A and 11B except for the collimators as indicated.

Figure 12A:
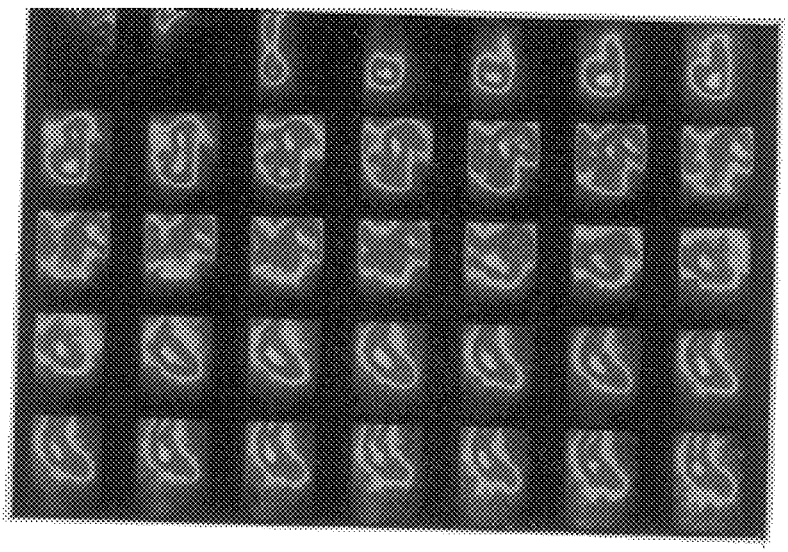
FIG. 12A shows an RNA study for a patient Quag using a conventional lead collimator and FIG. 12B shows an RNA study for patient Quag using a tin/lead collimator form of the invention.
Figure 12B:
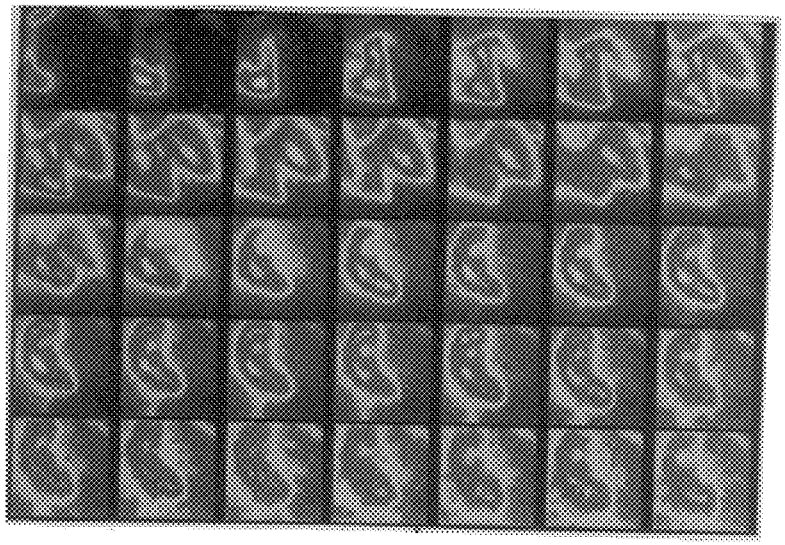

An RNA study was performed on patient Quag on Jun. 26, 1989 using the Conventional Lead Collimator on a conventional System 77 as is illustrated in FIG. 12A. FIG. 12B shows another RNA study of patient Quag performed Aug. 17, 1990 using a research model of the Tin/Lead Collimator on SIM400. The study concluded that the RV, LV and valve planes between RV and PA and between LV and AO are all better visualized in FIG. 12B compared to FIG. 12A and that the DA and onset of myocardial blush can be seen in FIG. 12B but not in FIG. 12A. This is an important comparison because FIG. 12A was performed on System 77 which has been the gold standard of RNA studies since 1972 and, until the research on SIM400 with the development of the Tin/Lead collimator, the System 77 represented the state of the art in First Pass collimators. The study parameters and protocols were essentially identical in both studies (FIGS. 12A and 12B). Both received the same image processing treatment on a SIM400.

Figure 13A:
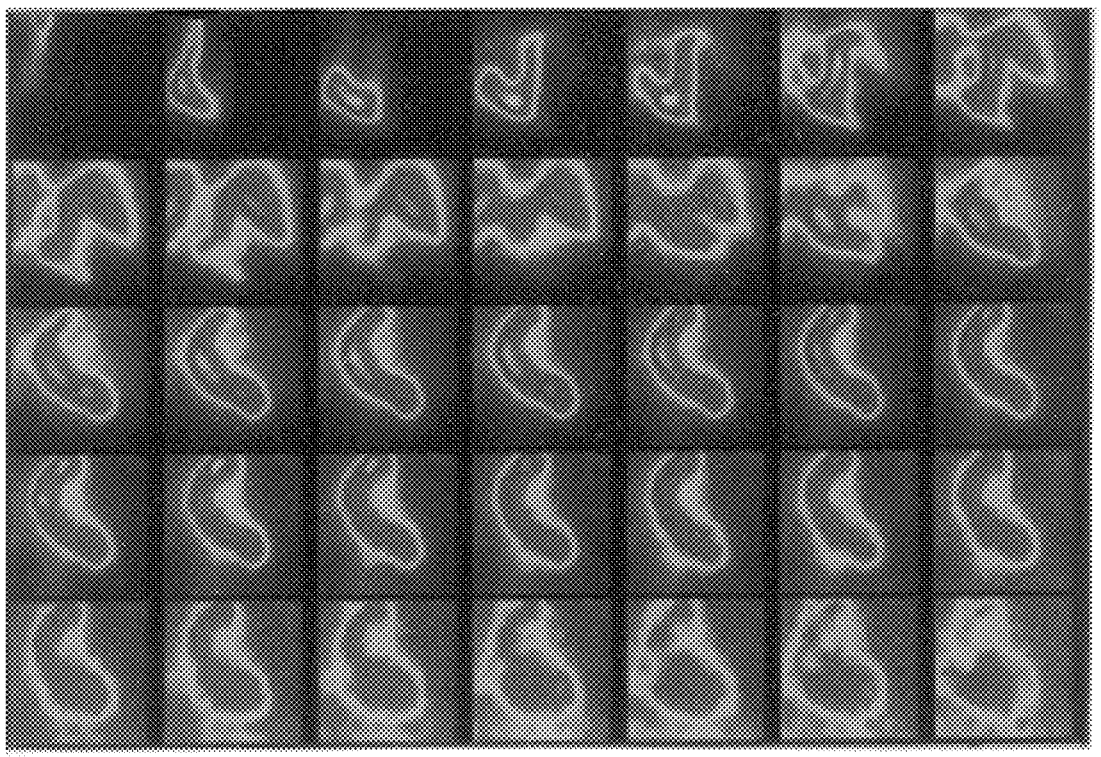
FIG. 13A shows an RNA study for a patient Chak using a high resolution lead collimator.
Figure 13B:
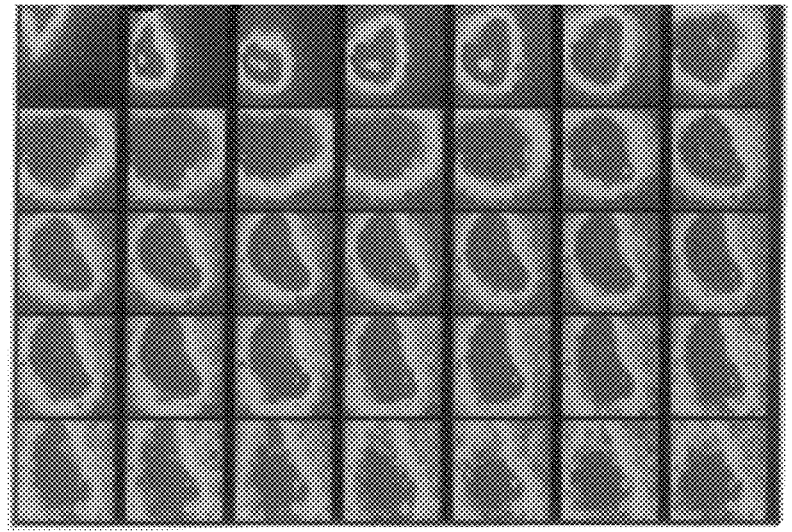
FIG. 13B shows a study for the patient performed using a simultaneous dual energy method.
Figure 13C:
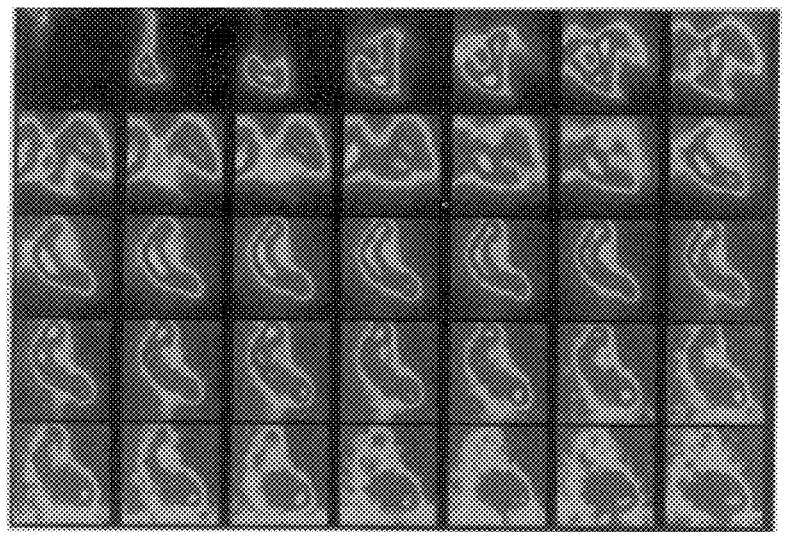
FIG. 13C shows an RNA study for the patient Chak using a tin/lead collimator form of the invention.

FIG. 13A shows data from a study performed on patient Chak in which a high spatial resolution dead collimator was used. Such collimators are not normally used in first pass studies because of its low efficiency. However, this study shows that spatial resolution alone cannot bring a first pass study to the quality achieved with the Tin/Lead collimator of FIG. 13C. The reason for this is shown in the Compton Scatter Image obtained in FIG. 13B. The data of FIG. 13B were obtained by performing a simultaneous dual energy study to allow a comparison of imaging a first pass RNA study with photopeak events and Compton Scatter and Pb X-ray events. This panel clearly shows the poor image quality that results from scatter and Pb X-ray events. The purpose of the Tin/Lead collimator is to reduce this imaging component. In FIG. 13C is shown an image produced in an RNA study performed on patient Chak on Aug. 17, 1990 using a Tin/Lead collimator. This study is superior to the photopeak study of FIG. 13A even when it is performed with the most highly optimized conventional lead collimator and high spatial resolution. It can be seen that the pure scatter/Pb X-ray image illustrated in this figure bears a tell-tale resemblance to the images shown using the conventional lead collimator.

Figure 14A:
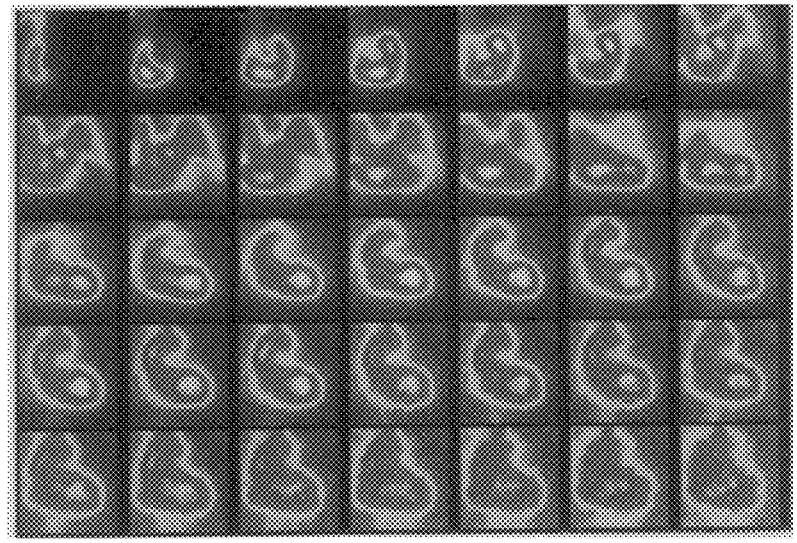
FIG. 14A shows an RNA study for a patient Mel using a conventional lead collimator and FIG. 14B shows an RNA study performed using a slow bolus mode with a tin/lead collimator form of the invention.
Figure 14B:
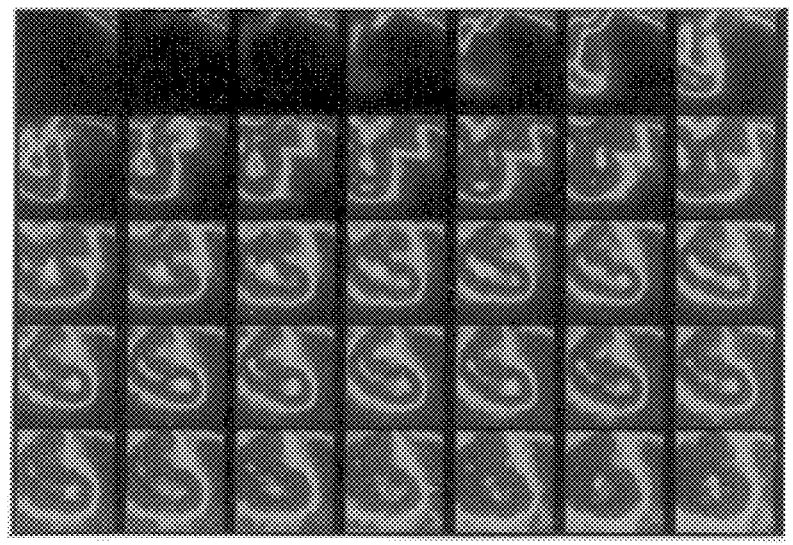

FIG. 14A is an image resulting from an RNA study performed on patient Mel on Jul. 31, 1989 using the conventional lead collimator on SIM400. FIG. 14B shows an image which was produced in a slow bolus study also performed on patient Mel on Sep. 4, 1990 using a research model of the Tin/Lead collimator on SIM400. The study concluded that FIGS. 14A and 14B are somewhat comparable in quality.

Preferably, in the collimator assembly 10 shown in FIGS. 1–3 the thin layer 22 does not have too high an atomic number, or the thin layer 22 can itself reemit a high energy X-ray which could be transmitted through the thin layer 22 and be sensed by the detector 34. Knowing the composition of the base structure 20, one can apply conventional radiation absorption knowledge and methods to determine the appropriate materials and their layer thicknesses necessary to absorb a substantial fraction of any inelastic scattered radiation, particularly emitted K alpha and L alpha X-rays from the base collimator structure 20.

The efficiency of the gamma ray collimator assembly 10 can be assessed with reasonable accuracy for the square cross section collimator geometry illustrated in FIG. 3. The efficiency is expressed in terms of the spatial dimensions:

$$E = A_1 A_2 / 4\pi l^2 M^2$$

$A_1$ = area of lead square (edge "b" squared)
$A_2$ = area of tin square (edge "a" squared)
P = longitudinal length of collimator passageway (see FIG. 2)
M = center to center spacing (see FIG. 2)

Thus, one can select a desired efficiency by adjusting the various geometries of the collimator assembly 10.

In another aspect of the invention the collimator assembly 10 can be constructed of any desired height and longitudinal length l along the collimator assembly 10. The user can then assemble a final collimator assembly 10 of any desired length of longitudinal passageway by stacking two or more different height collimator assemblies.

While preferred embodiments of the invention have been shown and described, it will be clear to those skilled in the art that various changes and modifications can be made without departing from the invention in its broader aspects as set forth in the provided hereinafter.

What is claimed is:

1. A gamma ray collimator assembly for use in a cardiac inspection system for resolving energetically unperturbed gamma rays emitted from a patient and for removing inelastic scattered gamma rays, comprising:

a plurality of collimator elements with each of said collimator elements having walls and each of said walls defining a plane, each of said walls absorbing said inelastic scattered gamma rays and said walls of each said collimator element defining an elongated longitudinal passageway having open ends through which the energetically unperturbed gamma rays enter and leave and said passageway comprised of a first material layer covered by a second material layer and the planes of said layers being parallel to a central longitudinal axis in each of said collimator elements said first material layer having a large absorption coefficient for said gamma Lays from the patient and said second material layer having a large absorption coefficient for said inelastically scattered gamma rays generated in said first material layer responsive to said gamma rays emitted from said patient.

2. The gamma ray collimator assembly as defined in claim 1 wherein said wall is comprised of lead with a thin tin layer disposed thereon.

3. The gamma ray collimator assembly as defined in claim 1 wherein said collimator assembly is comprised of a multiplicity of stacked, assembled collimator elements, each of said collimator elements aligned with a corresponding one of said collimator elements in the adjacent stacked plurality of collimator elements.

4. The gamma ray collimator assembly as defined in claim 3 wherein the longitudinal length of said longitudinal passageway for said stacked, assembled collimator elements is selected for a preferred resolution, gamma ray count rate and efficiency.

5. The gamma ray collimator as defined in claim 4 wherein the efficiency of detecting is defined by the formula, $$E = A_1 A_2 / 4\pi l^2 M^2$$

where $A_1$=area of lead square (edge squared)

$A_2$=area of tin square (edge squared)

$P$=longitudinal length of complete collimator passageway $M$=center to center spacing (face on) of adjacent collimator elements in each collimator stack.

6. The gamma ray collimator assembly as defined in claim 1 wherein each of said collimator elements comprises a square cross section lead tubing with an inner layer of a square cross section tin tubing.

7. The gamma ray collimator assembly as defined in claim 1 wherein said tin layer is deposited on said lead by at least one method of electroplating, evaporation, ion deposition and mechanical lamination of foil thereon.

8. A method of collimating energetically unperturbed radionuclide gamma radiation, comprising the steps of:

selecting a particular gamma ray radiation of energy $E_0$ for collimation, said gamma ray radiation being output from a specimen of interest;

positioning a detector of said gamma ray radiation in a location useful for gathering information about said specimen and associated with said gamma ray radiation; and using a collimator with each collimator element having a longitudinal passageway and a layered structure of walls with each of the walls defining a plane, said structure of walls having open ends through which the energetically unperturbed gamma radiation enters and leaves and including at least a first layer and second layer wherein divergent portions of said gamma ray radiation of energy $E_0$ are strongly absorbed by said first layer of said layered wall structure and with the planes of the layers being parallel to a central longitudinal axis in each said collimator element, the absorption of said gamma ray radiation by said first layer giving rise to inelastic scattered X-ray radiation of energy less than $E_0$ and said second layer having a large absorption coefficient for said inelastic scattered X-ray radiation.

9. The method as defined in claim 8 wherein said collimator comprises a first thin layer material disposed nearest the non divergent portion of said particular radiation passing through said longitudinal passageway with said first layer material having a high preferential absorption for said inelastic scattered spectra.

10. The method as defined in claim 8 wherein said layered wall structure comprises a thin tin layer on a base structure of lead.

11. A method of constructing a gamma ray collimator, comprising the steps of:

assembling a plurality of base lead collimator elements; and disposing a thin layer of tin on said lead collimator elements, said layer of tin being thick enough to preferentially absorb inelastic scattered X-rays arising from gamma rays striking said base lead collimator elements.

12. A method of constructing a gamma ray collimator for collimating gamma rays and passing energetically unperturbed gamma rays of energy $E_0$, comprising the steps of:

assembling a plurality of base lead collimator elements; and disposing a thin layer of tin on said lead collimator elements and forming a layered structure of walls with each of the walls defining a plane and said structure of walls forming open ends through which the unperturbed gamma rays enter and leave with the planes of the tin layer and lead collimator elements being parallel to a central longitudinal axis in each of said collimator elements, said layer of lead absorbing the $E_0$ gamma rays and the tin layer absorbing inelastic scattered X-rays arising from the $E_0$ gamma rays striking said base lead collimator elements.

13. The method as defined in claim 12 wherein selected ones of said stacked layers further include an inserted egg crating matrix with each longitudinally extending wall of said matrix comprised of a lead center portion with a thin inner tin layer disposed thereon.

14. The method as defined in claim 11 further including the step of inserting an egg crating matrix into said plurality of collimator elements to provide additional resolution.

15. A collimator assembly for use in an angiographic inspection system for resolving energetically unperturbed energy radiation of energy $E_0$ emitted from a patient and for removing perturbed, inelastic scattered radiation, comprising:

a plurality of collimator elements forming said collimator assembly with each of said collimator elements having walls and each of said walls defining a plane and said walls further forming open ends through which the energetically unperturbed radiation enters and leaves, and each of said walls of each collimator element absorbing some of said radiation entering said walls and said walls giving rise to emission of said inelastic scattered radiation having energy less than said energetically unperturbed radiation of energy $E_0$; and said walls further defining an elongated longitudinal passageway for each of said collimator elements and said walls comprised of a first material layer covered by a layer of a second material layer and the planes of said layers being parallel to a central longitudinal axis in each of said collimator elements, said first material layer having a large absorption coefficient for the gamma rays of energy $E_0$ and said second material layer having a large absorption coefficient for said perturbed, inelastically scattered radiation emitted from said first material responsive to said energetically unperturbed radiation of energy $E_0$ being absorbed by said walls.

16. The method as defined in claim 8 wherein said method is applied to performing gated first pass angiography.

* * * * *